United States Patent [19]

Peake et al.

[11] Patent Number: 4,950,666
[45] Date of Patent: Aug. 21, 1990

[54] DIFLUOROALKANE AND DIFLUOROALKENYLALKANE PESTICIDES

[75] Inventors: Clinton J. Peake, Trenton; Thomas G. Cullen, Milltown; Anthony J. Martinez, Hamilton Square, all of N.J.

[73] Assignee: FMC Corporation, Philadelphia, Pa.

[21] Appl. No.: 331,563

[22] Filed: Mar. 30, 1989

[51] Int. Cl.$^5$ ............ A01N 37/02; A01N 37/18; C07C 69/63; C07C 103/127
[52] U.S. Cl. ............ 514/227.5; 260/404.5; 260/408; 544/58.4; 546/245; 546/292; 546/309; 548/571; 549/76; 549/77; 549/79; 549/321; 549/323; 549/426; 549/466; 549/493; 558/444; 558/445
[58] Field of Search ............ 560/219, 227, 139, 142, 560/145; 562/598, 605; 564/204, 207, 208, 209, 210, 211, 212, 213, 214; 260/404.5, 408; 544/58.4; 546/245, 292, 309; 548/571; 549/76, 77, 79, 321, 323, 426, 466, 493; 558/444, 445; 514/227.5, 315, 345, 352, 423, 438, 461, 469, 471, 527, 528, 546, 549, 552, 558, 559, 560, 627, 628

[56] References Cited

U.S. PATENT DOCUMENTS 3,080,405 3/1963 Larsen et al. ............ 260/408
4,603,147 7/1986 Peake et al. ............ 514/743

FOREIGN PATENT DOCUMENTS 0228222 8/1987 European Pat. Off. .
0247484 12/1987 European Pat. Off. .

OTHER PUBLICATIONS

Abstract EP-247484 (1987).
Briggs et al., "Some Fluorine Containing Pheromone Analogues" Pestic. Sci. 1986, 17, 441-448.
Paleta et al., Chemical Abstracts, vol. 110, (1988 172678h.
Molines et al., Chemical Abstracts, vol. 109 (1987) 37955k.
Leroy et al., Chemical Abstracts, vol. 106 (1987) 67027g.

Primary Examiner—Richard L. Raymond
Attorney, Agent, or Firm—Stanford M. Back; Robert L. Andersen; H. Robinson Ertelt

[57] ABSTRACT

The present invention discloses compounds of the formula

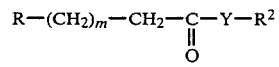

in which R is a 1,1-difluoroalkyl group or a 1,1-difluoroethenyl group having an even numbered carbon chain length of from 4 to 22 carbon atoms, pesticidal compositions thereof; and their use to control plant pests such as insects, acarids, and nematodes.

12 Claims, No Drawings

DIFLUOROALKANE AND DIFLUOROALKENYLALKANE PESTICIDES

The present invention relates to certain acid, acid salt, amide, and ester derivatives of difluoroalkanes or difluoroalkenylalkanes, formulated compositions thereof, and their use to control pests that prey on agricultural crops, such as insects, acarids, and nematodes.

The compounds of this invention are difluoroalkane or difluoroalkenylalkane derivatives of the structural formula I

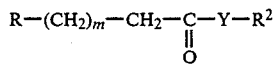

In formula I, R is a 1,1-difluoroalkyl group of 1 to 3 carbon atoms or a 1,1-difluoroalkenyl group of 2 to 4 carbon atoms, optionally carrying a halogen substituent selected from bromine and chlorine. The R group may be, for example, $F_2XC$, $F_2XCX^1CH$, $F_2XCCH_2X^1CH$, $F_2C=CX^2$, $F_2XCCH=CH$, or $F_2XCCH=CHX^1CH$ in which $X^2$ is hydrogen, bromine or chlorine and X and $X^1$ are bromine or chlorine. Of these, $F_2C=CH$ is the preferred group.

In formula I, m is an integer which produces a carbon chain length for the group $R(CH_2)_m$ which is an even number in the range of 2 to 20, Y is $-NR^1-$, or $-O-$, and $R^1$ is hydrogen or lower alkyl.

$R^2$ may be a wide variety of subtituents including:

(a) hydrogen, an alkali metal, or ammonium,
(b) alkyl of 1 to 12 carbon atoms,
(c) lower alkyl substituted with halogen, trifluoromethyl, ethenyl, difluoroethenyl ethynyl, lower alkoxy, $C_3$–$C_6$ cycloalkyl which may be fluoro-substituted, lower alkylcarbonyl, lower alkoxycarbonyl, hydroxycarbonyl, cyano, phenylmethylfuryl, phenoxy, halophenoxy, phenyl, halophenyl, $C_1$–$C_2$ alkoxyphenyl, thienyl, halothienyl, or a cyclopropyl group and a phenyl group which may be substituted with a substituent selected from halogen, methyl, trifluoromethyl and trifluoromethoxy, or a methyl group substituted with phenylmethyl and hydroxycarbonyl,
(d) phenyl which may be substituted with one to three substituents independently selected from lower alkyl, halogen, lower alkoxy, formyl, nitro, hydroxycarbonylethenyl, lower alkoxycarbonylethenyl, and lower alkylamino(lower)alkoxycarbonyl,
(e) pyridyl which may be substituted with halogen,
(f) a group of the formula $-SO_2R^3$ in which $R^3$ is phenyl or phenylmethyl in which the ring may be substituted with a substituent selected from the group consisting of lower alkyl, halogen, and lower alkoxy, thienyl, pyridyl, or lower alkyl,
(g) a group of the formula $-N=CR^4R^5$ in which $R^4$ is amino and $R^5$ is phenyl or phenylmethyl optionally ring substituted with lower alkoxy or trifluoromethoxy, or thienyl,
(h) a group of the formula $-C(SR^6)=NR^7$ in which $R^6$ is lower alkyl or $F_2C=CFC_2H_4$ and $R^7$ is lower alkylcarbonyl or phenyl which may be substituted with a halogen atom,
(i) a group of the formula $-NR^8R^9$ in which $R^8$ is hydrogen or lower alkyl, $R^9$ is hydrogen, lower alkyl, lower alkylaminocarbonyl, phenylcarbonyl, $F_2C=CH(CH_2)_3C(O)-$ or acetyl,
(j) a substituent selected from fluoroethoxy, $F_2ClCCH=CH(CH_2)_9$, $F_2C=CH(CH_2)_{10}$, 2,2-dimethyl-2,3-dihydrobenzofuranyl, 2,2-dimethyl-2,3-dihydrobenzofuranyloxycarbonyl, dimethoxyindanyl, and

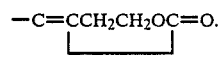

In addition, Y and $R^2$ taken together may be hydrogen or form a nitrogen containing group selected from di(lower)alkenylamino, piperidyl, pyrrolidinyl, or thiomorpholinyl.

In the foregoing description the term lower as applied to a hydrocarbyl group means an unsubstituted saturated group of 1 to 6 contiguous carbon atoms, preferably 1 to 4 carbon atoms, most preferably 1 or 2 carbon atoms; alkyl means a straight or branched chain hydrocarbon; halogen means bromine, chlorine or fluorine; and halo as applied to another group means that one or more hydrogen atoms of such other group have been replaced with a like number of halogen atoms.

As indicated above the preferred compounds are those in which R is $F_2C=CH-$. These compounds are illustrated by the compounds specifically set forth in Table 1:

TABLE 1

$F_2C=CH-(CH_2)_m-CH_2-\underset{\underset{O}{\|}}{C}-Y-R^2$

| No. | m | Y | $R^2$ |
|---|---|---|---|
| 44 | 0 | O | H |
| 194 | 2 | O | H |
| 138 | 4 | O | H |
| 139 | 6 | O | H |
| 191 | 8 | O | H |
| 61 | 10 | O | H |
| 45 | 0 | NH | H |
| 40 | 8 | NH | H |
| 70 | 0 | O | Na$^+$ |
| 80 | 8 | O | Na$^+$ |
| 67 | 0 | O | Li$^+$ |
| 72 | 0 | O | NH$_4^+$ |
| 183 | 12 | O | CH$_3$ |
| 15 | 8 | O | CH$_3$ |
| 197 | 0 | O | C$_2$H$_5$ |
| 193 | 2 | O | C$_2$H$_5$ |
| 112 | 8 | O | C$_2$H$_5$ |
| 184 | 10 | O | C$_2$H$_5$ |
| 180 | 8 | NC$_2$H$_5$ | C$_2$H$_5$ |
| 81 | 8 | NCH$_3$ | C$_2$H$_5$ |
| 114 | 8 | O | i-C$_3$H$_7$ |
| 86 | 8 | NH | i-C$_3$H$_7$ |
| 165 | 2 | NH | c-propyl |
| 84 | 8 | NH | c-propyl |
| 121 | 8 | O | c-propyl |
| 83 | 8 | NH | C$_4$H$_9$ |
| 65 | 0 | NH | i-C$_4$H$_9$ |
| 147 | 4 | NH | i-C$_4$H$_9$ |
| 200 | 2 | O | s-C$_4$H$_9$ |
| 93 | 4 | O | s-C$_4$H$_9$ |
| 127 | 8 | NH | s-C$_4$H$_9$ |
| 185 | 10 | NH | s-C$_4$H$_9$ |
| 186 | 12 | NH | s-C$_4$H$_9$ |
| 195 | 2 | O | t-C$_4$H$_9$ |
| 99 | 8 | O | t-C$_4$H$_9$ |
| 88 | 8 | NH | t-C$_4$H$_9$ |
| 110 | 8 | O | c-pentyl |
| 160 | 2 | NH | i-pent-2-yl |
| 164 | 2 | NH | c-pentyl |
| 87 | 8 | NH | c-pentyl |
| 119 | 8 | O | C$_6$H$_{13}$ |
| 117 | 8 | O | c-hexyl |
| 58 | 8 | O | C$_7$H$_{15}$-3-yl |

TABLE 1-continued

| | | | |
|---|---|---|---|
| 94 | 2 | O | $C_{11}H_{23}$ |
| 122 | 8 | O | $ClCH_2CH_2-$ |
| 118 | 8 | O | $(FCH_2)_2CH-$ |
| 68 | 0 | NH | $F_3CCH_2-$ |
| 156 | 2 | NH | $F_3CCH_2-$ |
| 144 | 4 | NH | $F_3CCH_2-$ |
| 149 | 6 | NH | $F_3CCH_2-$ |
| 101 | 8 | NH | $F_3CCH_2-$ |
| 187 | 12 | NH | $F_3CCH_2-$ |
| 82 | 8 | NH | $CH_2=CHCH_2-$ |
| 64 | 0 | O | $F_2C=CHC_2H_4-$ |
| 46 | 8 | O | $F_2C=CHC_4H_8-$ |
| 166 | 2 | NH | $HC\equiv CCH_2-$ |
| 85 | 8 | NH | $CH_3OC_2H_4-$ |
| 105 | 8 | NH | $C_2H_5OC_3H_6-$ |
| 116 | 8 | O | $\underline{c}\text{-}C_5H_9CH_2-$ |
| 159 | 2 | O | $\underline{c}\text{-}C_6F_{11}CH_2-$ |
| 124 | 8 | O | $CH_3C(O)CH_2-$ |
| 113 | 8 | O | $C_2H_5O_2CCH_2-$ |
| 126 | 9 | NH | $CH_3O_2CCHCH(CH_3)_2$ (substituent on CH) |
| 125 | 8 | NH | $CH_3O_2CCH_2-$ |
| 176 | 8 | NH | $HO_2CCHCH_3$ |
| 120 | 8 | O | $HO_2CCH_2-$ |
| 28 | 8 | NH | $HO_2CCH_2-$ |
| 27 | 8 | NH | $HO_2CC_3H_6-$ |
| 168 | 8 | NH | $HO_2CCHCH(CH_3)_2$ |
| 177 | 8 | NH | $HO_2CCHCH_2CH(CH_3)_2$ |
| 131 | 8 | NH | $CNCH_2-$ |
| 163 | 2 | NH | $CNCH_2-$ |
| 123 | 8 | O | $CNC_2H_4-$ |
| 50 | 0 | O | 5-benzyl-3-furylmethyl |
| 115 | 8 | O | $PhOC_2H_4-$ |
| 137 | 8 | O | $4\text{-}ClPhOC_2H_4-$ |
| 111 | 8 | O | $PhC_2H_4-$ |
| 109 | 8 | O | $PhCH_2-$ |
| 130 | 8 | NH | $PhCH_2-$ |
| 47 | 0 | O | $4\text{-}ClPhCH_2-$ |
| 2 | 8 | O | $4\text{-}ClPhCH_2-$ |
| 51 | 8 | NH | $4\text{-}ClPhCH_2-$ |
| 52 | 8 | O | $2\text{-}FPhCH_2-$ |
| 96 | 8 | O | $2,6\text{-}F_2PhCHCH_3$ |
| 9 | 8 | O | $2,3\text{-}F_2PhCHCH_3$ |
| 53 | 8 | O | $2\text{-}(CH_3O)PhCH_2-$ |
| 3 | 8 | O | $3\text{-}(CH_3O)PhCH_2-$ |
| 4 | 8 | O | $4\text{-}(CH_3O)PhCH_2-$ |
| 152 | 2 | NH | $ThCH_2-$ |
| 145 | 4 | NH | $ThCH_2-$ |
| 150 | 6 | NH | $ThCH_2-$ |
| 102 | 8 | NH | $ThCH_2-$ |
| 97 | 8 | O | $ThCHCH_3$ |
| 8 | 8 | O | $ThCHCH_3$ |
| 107 | 8 | NH | $5\text{-}ClThCH_2-$ |
| 7 | 8 | O | $5\text{-}ClThCH_2-$ |
| 13 | 8 | O | $(4\text{-}CF_3Ph)CH(\underline{c}\text{-}Pr)CH_2-$ |
| 11 | 8 | O | $(4\text{-}ClPh)CH(\underline{c}\text{-}Pr)CH_2-$ |
| 12 | 8 | O | $(4\text{-}CH_3Ph)CH(\underline{c}\text{-}Pr)CH_2-$ |
| 14 | 8 | O | $(4\text{-}CF_3OPh)CH(\underline{c}\text{-}Pr)CH_2-$ |
| 174 | 8 | NH | $PhCH_2CHCOOH$ |
| 129 | 8 | NH | $Ph-$ |
| 132 | 8 | $NCH_3$ | $Ph-$ |
| 170 | 8 | NH | $2\text{-}CH_3Ph-$ |
| 135 | 8 | NH | $2,6\text{-}(CH_3)_2Ph-$ |
| 73 | 0 | NH | $2,6\text{-}(iPr)_2Ph-$ |
| 74 | 2 | NH | $2,6\text{-}(iPr)_2Ph-$ |
| 151 | 2 | NH | $2\text{-}ClPh-$ |
| 158 | 2 | NH | $4\text{-}ClPh-$ |
| 92 | 4 | O | $2\text{-}ClPh-$ |
| 143 | 4 | NH | $2\text{-}ClPh-$ |
| 146 | 4 | NH | $4\text{-}ClPh-$ |
| 141 | 6 | NH | $2\text{-}ClPh-$ |
| 192 | 8 | NH | $2\text{-}ClPh-$ |
| 189 | 8 | NH | $3\text{-}ClPh-$ |
| 190 | 8 | NH | $4\text{-}ClPh-$ |
| 49 | 0 | NH | $2,4\text{-}Cl_2Ph-$ |
| 157 | 2 | NH | $2,4\text{-}Cl_2Ph-$ |
| 148 | 6 | NH | $2,4\text{-}Cl_2Ph-$ |
| 6 | 8 | NH | $3,4\text{-}Cl_2Ph-$ |
| 134 | 8 | NH | $2,4\text{-}Cl_2Ph-$ |
| 63 | 8 | O | $-Ph; 2,6\text{-}(CH_3O)_2, 4\text{-}(CH=CHCO_2CH_3)$ |
| 62 | 8 | O | $-Ph; 2,6\text{-}(CH_3O)_2, 4\text{-}(CH=CHCO_2H)$ |
| 59 | 8 | O | $-Ph; 2,6\text{-}(CH_3)_2, 4\text{-}CHO$ |
| 153 | 2 | NH | $-Ph; 2\text{-}Br, 4\text{-}NO_2$ |
| 5 | 8 | NH | $4\text{-}[(C_2H_5)_2NC_2H_4O_2C]Ph-$ |
| 48 | 0 | NH | $3\text{-}Pyr-$ |
| 142 | 4 | NH | $3\text{-}Pyr-$ |
| 140 | 6 | NH | $3\text{-}Pyr-$ |
| 103 | 8 | NH | $3\text{-}Pyr-$ |
| 95 | 10 | NH | $3\text{-}Pyr-$ |
| 128 | 8 | NH | $2\text{-}Cl\text{-}3\text{-}Pyr-$ |
| 23 | 8 | NH | $PhSO_2-$ |
| 171 | 8 | $NC_3H_7$ | $PhSO_2-$ |
| 173 | 8 | NH | $PhCH_2SO_2-$ |
| 178 | 8 | $NC_2H_5$ | $PhCH_2SO_2-$ |
| 182 | 8 | $NC_4H_9$ | $PhCH_2SO_2-$ |
| 181 | 8 | $NC_3H_7$ | $PhCH_2SO_2-$ |
| 179 | 8 | $NCH_3$ | $PhCH_2SO_2-$ |
| 17 | 8 | NH | $4\text{-}CH_3PhSO_2-$ |
| 22 | 8 | $NCH_3$ | $4\text{-}CH_3PhSO_2-$ |
| 26 | 8 | $NC_2H_5$ | $4\text{-}CH_3PhSO_2-$ |
| 30 | 8 | $NC_4H_9$ | $4\text{-}CH_3PhSO_2-$ |
| 29 | 8 | $NCH_3$ | $4\text{-}ClPhSO_2-$ |
| 172 | 8 | NH | $3\text{-}ClPhSO_2-$ |
| 16 | 8 | NH | $4\text{-}ClPhSO_2-$ |
| 25 | 8 | NH | $2\text{-}ClPhSO_2-$ |
| 21 | 8 | NH | $4\text{-}(CH_3O)PhSO_2-$ |
| 169 | 8 | $NC_2H_5$ | $4\text{-}ClPhSO_2-$ |
| 167 | 8 | $NC_3H_7$ | $4\text{-}CH_3PhSO_2-$ |
| 175 | 8 | NH | $ThSO_2-$ |
| 24 | 8 | NH | $3\text{-}PyrSO_2-$ |
| 18 | 8 | NH | $CH_3SO_2-$ |
| 19 | 8 | $NC_2H_5$ | $CH_3SO_2-$ |
| 69 | 0 | O | $PhC=N-$ with $NH_2$ |
| 78 | 0 | O | $4\text{-}(CH_3O)PhCH_2C=N-$ with $NH_2$ |
| 75 | 2 | O | $4\text{-}(CH_3O)PhCH_2C=N-$ with $NH_2$ |
| 76 | 2 | O | $4\text{-}(CF_3O)PhC=N-$ with $NH_2$ |

TABLE 1-continued

| No. | m | | |
|---|---|---|---|
| 71 | 0 | O | 4-(CF$_3$O)PhC=N—<br>$\|$<br>NH$_2$ |
| 77 | 0 | O | ThC=N—<br>$\|$<br>NH$_2$ |
| 106 | 8 | NH | (CH$_3$)$_3$CC(O)N=C—<br>$\|$<br>F$_2$C=CFC$_2$H$_4$S |
| 54 | 8 | NH | 4-ClPhN=C—<br>$\|$<br>SCH$_3$ |
| 39, 38 | 8 | NH | —NH$_2$ |
| 133 | 8 | NH | —N(CH$_3$)$_2$ |
| 43 | 8 | NH | CH$_3$NHC(O)NH— |
| 162 | 2 | NC(CH$_3$)$_3$ | PhC(O)NH— |
| 161 | 2 | NC(CH$_3$)$_3$ | F$_2$C=CHC$_3$H$_6$C(O)NH— |
| 41 | 8 | NH | CH$_3$C(O)NH— |
| 198, 104 | 8 | NCH$_3$ | FC$_2$H$_4$O— |
| 56 | 8 | O | F$_2$ClCCH=CHC$_9$H$_{18}$— |
| 115 | 2 | O | 2,2-dimethyl-2,3-dihydrobenzofuran-7-yl- |
| 55 | 8 | O | F$_2$C=CHC$_{10}$H$_{20}$— |
| 98 | 8 | O | 2,2-dimethyl-2,3-dihydrobenzofuran-7-yl |
| 154 | 2 | NH | 2,2-dimethyl-2,3-dihydrobenzofuran-7-yl-oxycarbonyl |
| 1 | 8 | O | 5,6-(CH$_3$O)$_2$indan-1-yl |
| 20 | 8 | O | —C=C(CH$_2$)$_2$OC=O<br>$\|$_____$\|$ |

| No. | m | YR$^2$ |
|---|---|---|
| 42 | 8 | H |
| 66 | 0 | —N(CH$_2$CH=CH$_2$)$_2$ |
| 91 | 8 | —N(CH$_2$CH=CH$_2$)$_2$ |
| 136 | 8 | —N(CH$_2$)$_4$CH$_2$<br>$\|$_____$\|$ |
| 89 | 8 | —N(CH$_2$)$_3$CH$_2$<br>$\|$_____$\|$ |
| 90 | 8 | —N(CH$_2$)$_2$SCH$_2$CH$_2$<br>$\|$_____$\|$ | c = cyclo
i = iso
s = secondary
t = tertiary
Ph = Phenyl, Th = Thien-2-yl
Pyr = pyridyl The following examples illustrate preparation of these compounds.

EXAMPLE 1

Synthesis of N-(2-Chlorophenyl)-12,12-Difluoro-111-Dodecenamide (Compound 192)

Step A Synthesis of 11-bromoundecanoic acid chloride as an intermediate

This compound was prepared using 23.9 grams (0.09 mole) of 11-bromoundecanoic acid and 9.9 ml (0.135 mole) of thionyl chloride.

Step B Synthesis of methyl 11-bromoundecanoate as an intermediate

With cooling and stirring, 4.0 ml (0.099 mole) of methanol was added to 25.6 grams (0.090 mole) of 11-bromoundecanoic acid chloride. Triethylamine, 13.8 ml (0.099 mole) was then added dropwise. Upon completion of addition the reaction mixture was allowed to warm to ambient temperature where it stirred for 16 hours. The reaction mixture was diluted with diethyl ether and was washed in turn with water, an aqueous solution saturated with sodium bicarbonate, water, and an aqueous solution saturated with sodium chloride. The organic layer was dried with sodium sulfate and filtered. The filtrate was concentrated under reduced pressure yielding 23.9 grams of methyl 11-bromoundecanoate. The nmr spectrum was consistent with the proposed structure.

Step C Synthesis of methyl 11-(4-methylphenylsulfonyloxy)undecanoate as an intermediate A mixture of 14.4 grams (0.052 mole) of silver para-toluenesulfonate in 130 ml of acetonitrile was stirred, and 11.3 qrams (0.041 mole) of methyl 11-bromoundecanoate was added dropwise. Upon completion of addition the reaction mixture stirred at ambient temperature for 16 hours. The reaction mixture was warmed to 40° C. where it stirred for eight hours and then it was warmed to 80° C. where it was stirred for an additional 16 hours. The reaction mixture was cooled to ambient temperature and poured into 600 ml of ice-water. The mixture was stirred until the ice melted and then was extracted with three portions of diethyl ether. The combined extracts were washed with four portions of water followed by two portions of an aqueous solution saturated with sodium chloride. The organic layer was dried with sodium sulfate and filtered. The filtrate was concentrated under reduced pressure yielding 14.6 grams of methyl 11-(4-methylphenylsulfonyloxy)undecanoate. The nmr spectrum was consistent with the proposed structure.

Step D Synthesis of Methyl 11-oxoundecanoate as an intermediate

Dimethylsulfoxide, 178 ml, was heated to 150° C. as nitrogen was bubbled through it. Sodium bicarbonate, 23.7 grams (0.282 mole), was added portionwise while maintaining the reaction mixture temperature at 140°-160° C. Upon completion of addition, 13.6 grams (0.037 mole) of methyl 11-(4-methylphenylsulfonyloxy)undecanoate was added portionwise during a ten minute period. Upon completion of addition the reaction mixture was allowed to cool to ambient temperature, and then it was poured into 600 ml of ice-water. The mixture was stirred until the ice melted, and then it was extracted with three portions of heptane. The combined extracts were washed with three portions of water followed by two portions of an aqueous solution saturated with sodium chloride. The organic layer was dried with sodium sulfate and filtered. The filtrate was concentrated under reduced pressure yielding 7.8 grams of methyl 11-oxoundecanoate. The nmr spectrum was consistent with the proposed structure.

Step E Synthesis of methyl 12,12-difluoro-11-dodecenoate

A stirred mixture of 7.5 grams (0.035 mole) of methyl 11-oxoundecanoate and 14.7 grams (0.07 mole) of dibromodifluoromethane was cooled to 0°-10° C., and a solution of 18.4 grams (0.07 mole) of triphenylphosphine in 50 ml of dimethylacetamide was added dropwise. During the addition the temperature of the reaction mixture was maintained at 0°-10° C. Upon completion of addition the reaction mixture was allowed to warm to ambient temperature, and 4.6 grams (0.07 mole) of zinc dust was added in two portions. The addition caused an exothermic reaction which raised the temperature of the reaction mixture to 90° C. The reaction mixture was allowed to cool to ambient temperature where it stood without stirring for 60 hours. The reaction mixture was diluted with water and was subjected to a steam distillation with pentane. The appropriate fractions were combined and concentrated under reduced pressure yielding 4.3 grams of methyl 12,12-difluoro-11-dodecenoate. The nmr spectrum was consistent with the proposed structure.

Step F Synthesis of 12,12-difluoro-11-dodecenoic acid

A mixture of 1.0 gram (0.004 mole) of methyl 12,12-difluoro-11-dodecenoate and 0.16 gram (0.004 mole) of powdered sodium hydroxide was stirred at ambient temperature for 16 hours. A few drops of water were added to the reaction mixture, and it was warmed to 75° C. where it stirred for 3–4 hours. The reaction mixture was cooled to ambient temperature, diluted with water and acidified to pH with aqueous 6N hydrochloric acid. The mixture was extracted with three portions of diethyl ether. The combined extracts were washed with an aqueous solution saturated with sodium chloride. The organic layer was dried with sodium sulfate and filtered. The filtrate was concentrated under reduced pressure yielding 0.9 gram of 12,12-difluoro-11-dodecenoic acid. The nmr spectrum was consistent with the proposed structure.

Step G Synthesis of N-(2-chlorophenyl)-12,12-difluoro-11-dodecenamide

With stirring 3.7 ml (0.05 mole) of thionyl chloride was added dropwise to 5.2 grams (0.022 mole) of 12,12-difluoro-11-dodecenoic acid. Upon completion of addition the reaction mixture stirred at ambient temperature for 16 hours, and then it was heated to 70° C. to remove the excess thionyl chloride under reduced pressure. The residual 12,12-difluoro-11-dodecenoic acid chloride was dissolved in 50 ml of toluene, and, in turn, 0.1 gram (catalyst) of 4-dimethylaminopyridine (DMAP), 3.2 grams (0.025 mole) of 2-chloroaniline, and 2.2 grams (0.022 mole) of triethylamine were added. Upon completion of addition the reaction mixture was stirred at ambient temperature for 60 hours. After this time the reaction mixture was shaken with 50 ml of water and 100 ml of diethyl ether. The water layer was removed, and the ether layer was in turn washed with 25 ml of aqueous 0.1N hydrochloric acid, 25 ml of water, 25 ml of an aqueous solution saturated with sodium bicarbonate, 25 ml of water, and 25 ml of an aqueous solution saturated with sodium chloride. The ether layer was dried with magnesium sulfate and filtered. The filtrate was concentrated under reduced pressure to a residue. The residue was recrystallized from ethanolwater yielding, in two crops, 5.7 grams of N-(2-chlorophenyl)-12,12-difluoro-11-dodecenamide; m.p. 54°–55° C. The nmr spectrum was consistent with the proposed structure.

EXAMPLE 2

Synthesis of 12,12-Difluoro-11-Docenoic Acid Hydrazide (Compound 38)

A stirred solution of 1.2 grams (0.024 mole) of hydrazine hydrate in 10 ml of ethanol was heated to reflux, and 3.0 grams (0.012 mole) of methyl 12,12-difluoro-11-dodecenoate was added dropwise. Upon completion of addition the reaction mixture was heated at reflux for four hours. After this time the reaction mixture was cooled to ambient temperature and filtered. The filtrate was concentrated under reduced pressure to form a residual solid. The solid was recrystallized from ethanol yielding 2.3 grams of 12,12-difluoro-11-dodecenoic acid hydrazide; m.p. 64°–66° C. The nmr spectrum was consistent with the proposed structure.

EXAMPLE 3

Synthesis of 12,12-Difluoro-11-Dodecenoic Acid 2-Acetylhydrazide (Compound 41)

A solution of 0.5 gram (0.002 mole) of 12,12-difluoro-11-dodecenoic acid hydrazide and 0.3 gram (0.003 mole) of triethylamine in 20 ml of diethyl ether was stirred, and 0.2 gram (0.003 mole) of acetyl chloride was added. The reaction mixture was stirred at ambient temperature for 30 minutes and was filtered. The filtrate was in turn washed with aqueous 10% hydrochloric acid, aqueous 10% sodium hydroxide, and an aqueous solution saturated with sodium chloride. The organic layer was dried with sodium sulfate and filtered. The filtrate was concentrated under reduced pressure yielding 0.4 gram of 12,12-difluoro-11-dodecenoic acid 2-acetylhydrazide. The nmr spectrum was consistent with the proposed structure.

EXAMPLE 4

Synthesis of N-Methyl-2-(12,12-Difluoro-11-Dodecenoyl)Hydrazinecarboxamide (Compound 43)

A stirred solution of 0.5 gram (0.002 mole) of 12,12-difluoro-11-dodecenoic acid hydrazide and 0.11 gram (0.002 mole) of methyl isocyanate in 30 ml of diethyl ether was heated under reflux for three hours. The reaction mixture was concentrated under reduced pressure yielding 0.5 gram of N-methyl-2-(12,12-difluoro-11-dodecenoyl)hydrazinecarboxamide. The nmr spectrum was consistent with the proposed structure.

EXAMPLE 5

Synthesis of 4,4-Difluoro-3-Butenoic Acid (Compound 44)

Step A Synthesis of 3-ethoxy-4-oxahexyl benzoate as an intermediate

A stirred solution of 50.0 grams (0.347 mole) of the sodium salt of benzoic acid and 53.0 grams (0.320 mole) of 3-ethoxy-4-oxahexyl chloride in 500 ml of dimethylformamide was heated at reflux for three hours. The reaction mixture was cooled to ambient temperature, and 500 ml of water was added. The mixture was extracted with two 700 ml portions of diethyl ether. The combined extracts were dried with sodium sulfate and filtered. The filtrate was concentrated under reduced pressure yielding 57.5 grams of 3-ethoxy-4-oxahexyl benzoate. The nmr spectrum was consistent with the proposed structure. Further extraction of the aqueous layer with diethyl ether yielded an additional 34.7 grams of the benzoate.

Step B Synthesis of 3-oxopropyl benzoate as an intermediate

A solution of 57.0 grams (0.226 mole) of 3-ethoxy-4-oxahexyl benzoate in 475 ml of tetrahydrofuran and 475 ml of aqueous 10% hydrochloric acid was stirred at ambient temperature for 18 hours. After this time the reaction mixture was stirred with 700 ml of diethyl ether. The organic layer was separated, washed with water, and then was dried with sodium sulfate. The mixture was filtered, and the filtrate was concentrated under reduced pressure yielding 28.0 grams of 3-oxopropyl benzoate. The nmr spectrum was consistent with the proposed structure.

Step C Synthesis of 4,4-difluoro-3-butenyl benzoate as an intermediate

This compound was prepared in a manner analogous to Example 1, Step E, using 10.0 grams (0.056 mole) of 3-oxopropyl benzoate, 23.4 grams (0.112 mole) of dibromodifluoromethane, 29.4 grams (0.112 mole) of triphenylphosphine, and 7.3 grams (0.112 mole) of zinc dust in 150 ml of dimethylacetamide. The yield of 4,4-difluoro-3-butenyl benzoate was 7.8 grams. The nmr spectrum was consistent with the proposed structure.

Step D Synthesis of 4,4-difluoro-3-butenol as an intermediate

A mixture of 7.5 grams (0.035 mole) of 4,4-difluoro-3-butenyl benzoate and 15 ml of aqueous 20% sodium hydroxide was placed in a reaction vessel equipped with a distillation head. With stirring, the reaction mixture was heated, causing the product 4,4-difluoro-3-butenol to separate by distillation. The yield of 4,4-difluoro-3-butenol was 2.7 grams; b.p. 75°–85° C. The nmr spectrum was consistent with the proposed structure.

Step E Synthesis of 4,4-difluoro-3-butenoic acid

A stirred solution of 0.9 gram (0.008 mole) of 4,4-difluoro-3-butenol in 20 ml of acetone was cooled to 20° C., and 6.3 ml (0.017 mole) of Jones Reagent was added dropwise (until the orange color persisted). A small amount of 1-methylethanol was added to destroy the excess Jones Reagent. The reaction mixture was passed through silica gel, and the eluant was concentrated under reduced pressure yielding 1.0 gram of 4,4-difluoro-3-butenoic acid. The nmr spectrum was consistent with the proposed structure.

EXAMPLE 6

Synthesis of 12-Chloro-12,12-Difluoro-10-Dodecenyl 12,12-Difluoro-11-Dodecenoate (Compound 56)

Step A Synthesis of 12,12-difluoro-11-dodecenoic acid chloride as an intermediate This compound was prepared using 2.8 grams (0.012 mole) of 12,12-difluoro-11-dodecenoic acid, 1.7 grams (0.013 mole) of oxalyl chloride, and two drops of dimethylformamide in 13 ml of methylene chloride. The yield of 12,12-difluoro-11-dodecenoic acid chloride was 3.2 grams. The nmr spectrum was consistent with the proposed structure.

Step B Synthesis of 10-bromo-12-chloro-12,12-difluorododecanol as an intermediate A 200 mL pressure bottle was purged with dry argon and 8.5 grams (0.05 mole) of 10-undecen-1-ol was added. This was followed by the slow addition of 1.0 gram (catalyst) of benzoyl peroxide. The mixture was cooled, and 16.5 grams (0.10 mole) of bromochlorodifluoromethane was added. The bottle was immediately sealed, and the reaction mixture was warmed to 60°–65° C. where it was stirred for 60 hours. After this time the reaction mixture was cooled in an ice-methanol bath for one hour. The bottle was opened, and the reaction mixture was taken up in 100 mL of pentane. The solution was washed in turn with one 50 mL portion of an aqueous solution saturated with sodium bicarbonate, two 50 mL portions of water, and one 50 mL portion of an aqueous solution saturated with sodium chloride. The organic layer was dried with magnesium sulfate and filtered. The filtrate was concentrated under reduced pressure yielding 13.5 grams of 10-bromo-12-chloro-12,12-difluorododecanol.

The nmr spectrum was consistent with the proposed structure. The reaction was repeated several times.

Step C Synthesis of 12-chloro-12,12-difluoro-10-dodecenol as an intermediate

The stirred intermediate 10-bromo-12-chloro-12,12-difluorododecanol, 31.9 grams (0.095 mole), was cooled, and 15.9 grams (0.11 mole) of 1,8-diazabicyclo[5.4.0]undec-7-ene (DBU) was added dropwise. Upon completion of addition the reaction mixture was allowed to warm to ambient temperature where it was stirred for 16 hours. After this time the reaction mixture was warmed to 70° C. where it was stirred for one hour. The reaction mixture was cooled, and then it was taken up in 200 mL of methylene chloride. The solution was washed in turn with one 150 mL portion of aqueous 1N hydrochloric acid, one 100 mL portion of water, one 100 mL portion of an aqueous solution saturated with sodium bicarbonate, one 100 mL portion of water, and one 100 mL portion of an aqueous solution saturated with sodium chloride. The organic layer was dried with magnesium sulfate and filtered. The filtrate was concentrated under reduced pressure to a residual oil. The oil was distilled under high vacuum yielding 14.3 grams of 12-chloro-12,12-difluoro-10-dodecenol, b.p. 130°–131° C./1.1–1.2 mm.

The nmr spectrum was consistent with the proposed structure.

Step D Synthesis of 12-chloro-12,12-difluoro-10-dodecenyl-12,12-difluoro-11-dodeoenoate This compound was prepared using 1.5 grams (0.006 mole) of 12,12-difluoro-11-dodecenoic acid chloride (prepared in Step A), 1.4 grams (0.005 mole) of 12-chloro-12,12-difluoro-10-dodecenol (prepared in Steps B and C), 1.0 ml (excess) of triethylamine, and a catalytic amount of 4-dimethylaminopyridine in 15 ml of diethyl ether. The yield of 12-chloro-12,12-difluoro-10-dodecenyl 12,12-difluoro-11-dodecenoate was 1.0 gram. The nmr spectrum was consistent with the proposed structure.

EXAMPLE 7

Synthesis of 12,12-Difluoro-11-Dodecenyl 12,12-Difluoro-11-Dodecenoate (Compound 55)

Step A Synthesis of 1,1-difluorododec-1,11-diene as an intermediate

This compound was prepared in a manner analogous to that of Example 1, Step E, using 67.3 grams (0.4 mole) of 10-undecenal, 73.0 grams (0.8 mole) of dibromodifluoromethane, 210.0 grams (0.8 mole) of triphenylphosphine and 52.6 grams (0.8 mole) of zinc dust in 600 mL of dimethylacetamide. The yield of 1,1-difluorododec-1,11-diene was 33.7 grams.

Step B Synthesis of 12,12-difluoro-11-dodecenol as an intermediate

With stirring, 14.5 grams (0.072 mole) of 1,1-difluorododec-1,11-diene was cooled to 0° C., and 25 ml (0.025 mole—1M in tetrahydrofuran) of borane·tetrahydrofuran complex was added dropwise. Upon completion of addition the reaction mixture was stirred for 30 minutes during which time the reaction mixture temperature was at 8°–12° C. After this time 25 ml of aqueous 3N sodium hydroxide was added dropwise. This was followed by 30 ml of aqueous 30% hydrogen peroxide. During the initial peroxide addition the exothermic reaction caused the reaction mixture temperature to rise to 30°-35° C. The reaction mixture was cooled to approximately 20° C., and the peroxide addition was continued. Upon completion of addition the reaction mixture was stirred at ambient temperature for 30 minutes, and then it was warmed to 45°-50° C. where it stirred for one hour. After this time it was allowed to cool to ambient temperature where it stood for 60 hours. The reaction mixture was shaken with 100 ml of water and 50 ml of methylene chloride. The methylene chloride layer was separated, and the water layer was extracted with two 50 ml portions of methylene chloride. The combined methylene chloride extracts were washed with 25 ml of water and 25 ml of an aqueous solution saturated with sodium chloride. The organic layer was dried with magnesium sulfate and filtered. The filtrate was concentrated under reduced pressure to a residue. The residue was distilled under reduced pressure yielding 7.6 grams of 12,12-difluoro-11-dodecenol; b.p. 80-85/0.2 mm. The nmr spectrum was consistent with the proposed structure.

Step C Synthesis of 12,12-difluoro-11-dodecenyl 12,12-difluoro-11-dodecenoate

This compound was prepared using 1.5 grams (0.0059 mole) of 12,12-difluoro-11-dodecenoic acid chloride, 1.2 grams (0.0054 mole) of 12,12-difluoro-11-dodecenol, 1.0 ml (excess) of triethylamine, and a catalytic amount of 4-dimethylaminopyridine in 15 ml of diethyl ether. The yield of 12,12-difluoro-11-dodecenyl 12,12-difluoro-11-dodecenoate was 1.6 grams. The nmr spectrum was consistent with the proposed structure.

The compounds of this invention exhibit excellent insecticidal and acaricidal activity when applied to the leaves and stems, that is the above ground portions of the plant. Some of the compounds of the invention exhibit systemic downward activity when so applied, thereby controlling soil-borne insects such as corn rootworm and nematodes. Numerous compounds also exhibit systemic upward activity when applied to the soil in the vicinity of the root zone in which plants are or are to be planted. Some of the compounds also exhibit symplastic (leaf to leaf systemic) activity when applied to the above ground portions of the plants. These properties are illustrated in the examples below.

The compounds of the present invention were tested for insecticidal and acaricidal activity against southern armyworm (*Spodoptera eridania*), Mexican bean beetle (*Epilachna varvestis*), cabbage looper (*Trichoplusia ni*), pea aphid (*Acyrthosiphon pisum*), tobacco budworm (*Heliothis virescens*), and twospotted spider mite (*Tetranychus urticae*).

In initial tests to determine activity against insects and acarids on foliage, 6-10 day old pinto bean (*Phaseolus vulgaris*) or fava bean (*Vicia faba*) plants were sprayed to runoff on both upper and lower leaf surfaces with 10% (v/v) acetone:water solutions of test chemical to provide an application rate of 1000 ppm. The 10% acetone-water solvent used to prepare the solutions of test chemical contained one drop of surfactant per 100 ml of solvent. Two plants for each insect species and test chemical were sprayed. The sprayed plants were transferred to a hood where they were kept until the spray had dried.

Two pinto bean plants treated with test chemical as described above were removed from their pots by cutting the stem just above the soil line. The excised leaves and stems from each plant were placed in individual 3-ounce paper cups. Ten third instar (10-12 days old) Mexican bean beetle (MBB) larvae or third instar (8-10 days old) southern armyworm (SAW) larvae were counted into each cup, a lid was placed on each cup, and the closed cup was then held for a 48 hour exposure period at 26° C. and 50% relative humidity. At the end of the 48 hour exposure period the cups were opened and the numbers of dead and live insects were counted. Moribund larvae which were disoriented or unable to crawl normally were counted as dead. Using the insect counts, the efficacy of the test chemical was expressed in percent mortality.

Two fava bean plants treated with test chemical as described above were each placed in their entirety, including the pot, into individual 48-ounce waxed paper containers. Ten adult pea aphids (PA) were counted into each container. A plastic dome lid was placed on each container which was then held for a 48-hour exposure period at 26° C. and 50% relative humidity. Efficacy of the test chemical was determined as previously described.

Leaves infested with adult twospotted spider mites (TSM-S) were removed from culture plants and cut into segments containing 50-75 female mites. Each segment was placed onto the upper leaf surface of a whole pinto bean plant. After the mites had migrated to the under surfaces of the leaves, the leaf segments used to infest were removed and each plant sprayed with test chemical as described above. After the plants had dried, the entire plant and pot were placed in a metal tray in a hood. A supply of water in the tray kept the plants turgid throughout a 48-hour exposure period at 26° C. under constant light.

Activity against twospotted spider mites was estimated by comparing the amount of feeding damage (silvery discoloration of leaf) and webbing on the test plants to the untreated check. Test plants with feeding damage and webbing equal to the check were considered inactive. Test plants that show reduced feeding damage or webbing were examined under a microscope at approximately 10X magnification. Only adult female mites on the underside of the leaf were counted. Percent mortality was calculated by dividing the number of dead mites by the total number of mites on the leaf.

Tests conducted with cabbage looper (CL) were done in the manner described for the Mexican bean beetle and southern armyworm. The test species were exposed to the treated plants either for a 48 hour or a 96 hour period.

The test with tobacco budworm (TBW) were conducted in the manner described above for Mexican bean beetle and southern armyworm, except that four replicates were used each of which used five second instar (4-5 days old) tobacco budworms.

The results of these tests utilizing a 48 hour exposure period and an application rate of 1000 ppm are shown in Table 2 below. In general the compounds of this invention exhibited excellent activity against several of the test species.

TABLE 2

| | RESULTS OF FOLIAR TESTS AGAINST INSECTS AND ACARIDS | | | | | |
|---|---|---|---|---|---|---|
| | | | % Kill | | | |
| Cmpd # | CL | MBB | PA | SAW | TBW | TSM-S |
| 1 | 70 | 100 | 75 | | | 100 |
| 2 | 70 | 95 | 85 | | | 100 |
| 3 | 70 | 95 | 90 | | | 100 |
| 4 | 35 | 95 | 100 | | | 100 |
| 5 | 55 | 100 | 40 | | | 100 |
| 6 | 60 | 90 | 0 | | | 100 |

TABLE 2-continued
RESULTS OF FOLIAR TESTS AGAINST INSECTS AND ACARIDS

| Cmpd # | CL | MBB | % Kill PA | SAW | TBW | TSM-S |
|---|---|---|---|---|---|---|
| 7 | 75 | 100 | 90 | | | 100 |
| 8 | 90 | 100 | 100 | | | 100 |
| 9 | 85 | 100 | 75 | | | 100 |
| 11 | 45 | 95 | 90 | | | 100 |
| 12 | 75 | 90 | 100 | | | 100 |
| 13 | 75 | 100 | 100 | | | 100 |
| 14 | 75 | 95 | 90 | | | 100 |
| 15 | 15 | 95 | 100 | | | 100 |
| 16 | 35 | 95 | 100 | | | 100 |
| 17 | 50 | 95 | 85 | | | 100 |
| 18 | 90 | 100 | 100 | | | 100 |
| 19 | 75 | 100 | 100 | | | 100 |
| 20 | 70 | 100 | 100 | | | 100 |
| 21 | 95 | 95 | 100 | | | 100 |
| 22 | 60 | 95 | 90 | | | 100 |
| 23 | 80 | 100 | 100 | | | 100 |
| 24 | 95 | 100 | 75 | | | 100 |
| 25 | 60 | 90 | 100 | | | 100 |
| 26 | 90 | 95 | 75 | | | 100 |
| 27 | 25 | | | 10 | 20 | |
| 28 | 70 | | | 0 | 41 | |
| 29 | 80 | | | 0 | 100 | |
| 30 | 90 | | | 0 | 100 | |
| 38 | 55 | 90 | 70 | | | 100 |
| 39 | 5 | 85 | 80 | | | 95 |
| 40 | 75 | 90 | 100 | | | 95 |
| 41 | 70 | 100 | 15 | | | 88 |
| 42 | 70 | 100 | 95 | | | 98 |
| 43 | 90 | 80 | 0 | | | 0 |
| 44 | 95 | 100 | 100 | | | 100 |
| 45 | 70 | 100 | 100 | | | 100 |
| 46 | 45 | 100 | 100 | | | 100 |
| 47 | 50 | | | 0 | 40 | |
| 48 | 70 | | | 0 | 26 | |
| 49 | 45 | | | 0 | 10 | |
| 50 | 50 | | | 0 | 49 | |
| 51 | 35 | 70 | 0 | | | 100 |
| 52 | 0 | 80 | 100 | | | 100 |
| 53 | 0 | 95 | 80 | | | 100 |
| 54 | 0 | 80 | 0 | | | 100 |
| 55 | 75 | 100 | 70 | | | 95 |
| 56 | 45 | 100 | 40 | | | 95 |
| 58 | 75 | 70 | 75 | | | 100 |
| 59 | 70 | 100 | 70 | | | 100 |
| 61 | 100 | 95 | 100 | | | 100 |
| 62 | 30 | 15 | 40 | | | 100 |
| 63 | 25 | 15 | 15 | | | 100 |
| 64 | 5 | 70 | 100 | | | 0 |
| 65 | 50 | 90 | 100 | | | 0 |
| 66 | 30 | 95 | 75 | | | 100 |
| 67 | 85 | 100 | 100 | | | 100 |
| 68 | 45 | 100 | 100 | | | 100 |
| 69 | 80 | 100 | 100 | | | 100 |
| 70 | 75 | 100 | 100 | | | 100 |
| 71 | 70 | 100 | 100 | | | 100 |
| 72 | 60 | 95 | 100 | | | 100 |
| 73 | 50 | 15 | 0 | | | 100 |
| 74 | 35 | 0 | 0 | | | 75 |
| 75 | 85 | 90 | 100 | | | 85 |
| 76 | 90 | 45 | 100 | | | 100 |
| 77 | 75 | 100 | 100 | | | 100 |
| 78 | 50 | 75 | 100 | | | 100 |
| 80 | 100 | | | 75 | 95 | |
| | 100 | 100 | 100 | | | 100 |
| 81 | 25 | | | 0 | 60 | |
| 82 | 55 | | | 75 | 95 | |
| 83 | 30 | | | 55 | 95 | |
| 84 | 25 | | | 60 | 79 | |
| 85 | 85 | | | 70 | 100 | |
| 86 | 95 | | | 75 | 71 | |
| 87 | 70 | | | 70 | 76 | |
| 88 | 40 | | | 25 | 90 | |
| 89 | 10 | | | 10 | 55 | |
| 90 | 25 | | | 15 | 18 | |
| 91 | 25 | | | 25 | 11 | |
| 92 | 50 | 80 | 100 | | | 100 |
| 93 | 25 | 20 | 100 | | | 100 |
| 94 | 10 | 0 | 100 | | | 100 |
| 95 | 95 | | | 45 | 90 | |
| 96 | 85 | 100 | 100 | | | 100 |
| 97 | 75 | 100 | 100 | | | 100 |
| 98 | 70 | 80 | 100 | | | 100 |
| 99 | 100 | 100 | 90 | | | 100 |
| 101 | 95 | 100 | 100 | | | 100 |
| 102 | 100 | 100 | 85 | | | 100 |
| 103 | 100 | 100 | 100 | | | 100 |
| 104 | 65 | 75 | 100 | | | 100 |
| 105 | 45 | 95 | 100 | | | 100 |
| 106 | 75 | 90 | 5 | | | 100 |
| 107 | 70 | 90 | 5 | | | 100 |
| 109 | 50 | 100 | 100 | | | 100 |
| 110 | 70 | 100 | 100 | | | 100 |
| 111 | 40 | 100 | 100 | | | 100 |
| 112 | 25 | 95 | 100 | | | 93 |
| 113 | 60 | 95 | 100 | | | 100 |
| 114 | 40 | 95 | 100 | | | 100 |
| 115 | 75 | 100 | 100 | | | 100 |
| 116 | 80 | 100 | 100 | | | 100 |
| 117 | 75 | 100 | 100 | | | 100 |
| 118 | 70 | 100 | 100 | | | 100 |
| 119 | 55 | 100 | 100 | | | 100 |
| 120 | 70 | 90 | 100 | | | 100 |
| 121 | 15 | 85 | 100 | | | 100 |
| 122 | 45 | 100 | 100 | | | 100 |
| 123 | 40 | 95 | 100 | | | 100 |
| 124 | 80 | 100 | 100 | | | 100 |
| 125 | 20 | 95 | 100 | | | 100 |
| 126 | 75 | 100 | 100 | | | 100 |
| 127 | 85 | 95 | 100 | | | 100 |
| 128 | 100 | 95 | 100 | | | 100 |
| 129 | 80 | 100 | 100 | | | 100 |
| 130 | 85 | 100 | 80 | | | 100 |
| 131 | 35 | 100 | 100 | | | 100 |
| 132 | 10 | 30 | 0 | | | 100 |
| 133 | 75 | 100 | 100 | | | 100 |
| 134 | 55 | 85 | 100 | | | 100 |
| 135 | 30 | 70 | 100 | | | 100 |
| 136 | 70 | 100 | 100 | | | 100 |
| 137 | 75 | 100 | 100 | | | 100 |
| 138 | 70 | 100 | 100 | | | 100 |
| 139 | 100 | 100 | 100 | | | 100 |
| 140 | 70 | 95 | 80 | | | 100 |
| 141 | 80 | 95 | 100 | | | 100 |
| 142 | 80 | 100 | 100 | | | 100 |
| 143 | 100 | 100 | 100 | | | 100 |
| 144 | 20 | 100 | 100 | | | 100 |
| 145 | 85 | 100 | 100 | | | 100 |
| 146 | 75 | 95 | 100 | | | 100 |
| 147 | 95 | | | 5 | 25 | |
| 148 | 75 | | | 0 | 38 | |
| 149 | 50 | | | 0 | 26 | |
| 150 | 100 | | | 0 | 33 | |
| 151 | 55 | 100 | 100 | | | 90 |
| 152 | 70 | 100 | 100 | | | 100 |
| 153 | 100 | 100 | 100 | | | 100 |
| 154 | 100 | 85 | 100 | | | 100 |
| 155 | 90 | 100 | 100 | | | 100 |
| 156 | 30 | | | 0 | 13 | |
| 157 | 95 | | | 0 | 61 | |
| 158 | 95 | | | 5 | 63 | |
| 159 | 95 | | | 0 | 35 | |
| 160 | 0 | 0 | 90 | | | 100 |
| 161 | 0 | | | 0 | 5 | |
| 162 | 40 | | | 10 | 26 | |
| 163 | 100 | | | 10 | 65 | |
| 164 | 100 | | | 70 | 70 | |
| 165 | 90 | | | 50 | 90 | |
| 166 | 95 | | | 45 | 85 | |
| 167 | 90 | | | 0 | 94 | |
| 168 | 80 | | | 5 | 94 | |
| 169 | 100 | | | 0 | 95 | |
| 170 | 100 | | | 0 | 100 | |
| 171 | 95 | | | 10 | 95 | |
| 172 | 90 | | | 15 | 100 | |

TABLE 2-continued
RESULTS OF FOLIAR TESTS AGAINST INSECTS AND ACARIDS

| Cmpd # | CL | MBB | % Kill PA | SAW | TBW | TSM-S |
|---|---|---|---|---|---|---|
| 173 | 90 | | | 5 | 100 | |
| 174 | 80 | | | 0 | 70 | |
| 175 | 65 | | | 10 | 100 | |
| 176 | 55 | | | 10 | 80 | |
| 177 | 50 | | | 15 | 100 | |
| 178 | 60 | | | 20 | 70 | |
| 179 | 100 | | | 50 | 100 | |
| 180 | 35 | | | 5 | 100 | |
| 181 | 90 | | | 5 | 95 | |
| 182 | 95 | | | 0 | 100 | |
| 183 | 75 | | | 0 | 92 | |
| 184 | 70 | | | 60 | 89 | |
| 185 | 85 | | | 30 | 100 | |
| 186 | 85 | | | 20 | 100 | |
| 187 | 85 | | | 75 | 100 | |
| 189 | 100 | | | 35 | 100 | |
| 190 | 55 | | | 45 | 100 | |
| 191 | 90 | | | 0 | 100 | |
| 192 | 100 | | | 0 | 100 | |
| 194 | 10 | 95 | 90 | | 100 | |
| 198 | 70 | 95 | 100 | | | 100 |
| 200 | 95 | 100 | | | | |

The compounds of the present invention were tested for insecticidal activity against southern corn rootworm in the soil. Tests were conducted against this species in the following manner:

A 0.25 mL aliquot of a stock solution containing 64 mg of technical candidate insecticide in 4.0 mL of acetone was pipetted into 41 mL of distilled water containing 0.1% octylphenoxypolyethoxyethanol emulsifier. The resultant solution had a concentration of 15 ppm.

Four mL of each test solution was pipetted into a 4 ounce specimen cup containing two two-day-old corn sprouts completely covered by 26 grams of dry sandy soil. The treated soil in each cup was allowed to stand uncovered in a hood to evaporate the acetone. Each cup was capped, and the soil in each cup was mixed thoroughly. The cap of each cup was removed, and ten second instar southern corn rootworm larvae were added to each cup. The cups were each covered with lids perforated with two small holes to allow for ventilation. The cups were then held under fluorescent light (12 hours light: 12 hours dark) at 24°-26° C. for 48 hours. An untreated check and an appropriate standard were included in each test. Two replicates were run for each chemical treatment.

The unaffected larvae from the soil of each cup were extracted by placing the contents of each cup into a modified Berlese polyethylene funnel fitted with an 18-mesh screen. The funnels were placed over containers of an aqueous detergent solution. Incandescent lights (100 watts) were placed 36 cm above the soil in each funnel. The heat from these lights slowly dried the soil causing larvae that had not been affected by the candidate insecticide to emerge from the soil and drop out of the funnel into the detergent solution. The percent mortality was determined by comparing the number of larvae in the detergent solution with the total number of larvae infested during the initiation of the test. The results utilizing a 48 hour exposure period and an application rate of 15 ppm, are shown in Table 3:

TABLE 3
Results of Soil Incorporated Tests Against the Southern Corn Rootworm

| Cmpd # | % Kill SCR | Cmpd # | % Kill SCR |
|---|---|---|---|
| 1 | 100 | 55 | 100 |
| 2 | 100 | 56 | 100 |
| 4 | 100 | 57 | 100 |
| 7 | 100 | 58 | 100 |
| 9 | 100 | 59 | 100 |
| 15 | 100 | 61 | 85 |
| 17 | 80 | 67 | 90 |
| 23 | 60 | 77 | 90 |
| | 100 | 80 | 95 |
| 38 | 100 | 92 | 95 |
| 40 | 100 | 93 | 95 |
| 42 | 100 | 96 | 100 |
| 43 | 100 | 97 | 100 |
| 44 | 100 | 98 | 100 |
| 45 | 100 | | |
| 49 | 70 | | |
| 99 | 100 | 125 | 55 |
| 101 | 100 | 126 | 65 |
| 104 | 100 | 128 | 80 |
| 110 | 95 | 138 | 55 |
| 112 | 100 | 139 | 65 |
| 114 | 65 | 147 | 60 |
| 115 | 95 | 151 | 60 |
| 116 | 100 | 154 | 55 |
| 119 | 60 | 157 | 65 |
| 120 | 80 | 173 | 80 |
| 121 | 75 | 191 | 75 |
| 123 | 85 | 194 | 85 |
| 124 | 95 | 200 | 80 |

In evaluations to determine the upward systemic insecticidal and acaricidal activity the compounds of the present invention were tested against the insect and acarid species previously described in the initial tests to determine insecticidal and acaricidal activity. The host plants for these insects and acarids were also the same as previously described.

Stock solutions of the test chemical were prepared by dissolving the appropriate amount of technical material in a minimum of acetone. Test solutions were then prepared by the serial dilution of aliquots of the stock solution with distilled water containing 0.1% of octylphenoxypolyethoxyethanol emulsifier.

Seven-day-old fava bean plants and seven- to ten-day-old pinto bean plants growing in 240 grams of a New Jersey sandy soil in individual 7.5 cm pots were each placed in 46 ounce paper containers. An appropriate amount of test solution, prepared above, was drenched evenly over the soil surface of each bean plant to provide a final test concentration in the soil ranging from 50 to 6.25 ppm. Care was taken not to wet the foliage or the stems of the bean plants. There were two replicates for each chemical treatment. Standards and untreated controls were included in each test. Following a two day translocation period, dry untreated sand was added to cover the soil in each pot. Ten insects were counted into each container, using the fava bean plants for the pea aphid and the pinto bean plants for the cabbage looper, Mexican bean beetle, southern armyworm, and tobacco budworm. Pinto bean plants were also used in the tests with the twospotted spider mites which were transferred to the test plants in the manner previously described. Upon completion of the infestation each of the 46 ounce containers was covered with a piece of nylon screen. Percent mortality was determined 48 hours after infestation using the methods previously described. The results, utilizing a 48 hour exposure period, are shown in Table 4:

TABLE 4

RESULTS OF SYSTEMIC (UPWARD) TESTS AGAINST INSECTS AND ACARIDS

| Cmpd # | Rate PPM | CL | MBB | PA | SAW | TBW | TSM-S |
|---|---|---|---|---|---|---|---|
| 1 | 50 | | | 10 | | | |
| 2 | 50 | | | 0 | | | |
| 3 | 25 | 65 | | | | | |
| 4 | 50 | | | 70 | | | |
| 5 | 50 | | | 0 | | | |
| 6 | 25 | | | | | 50 | |
| 8 | 50 | | | 0 | | | |
| 9 | 50 | | | 0 | | | |
| 12 | 10 | | | 10 | | | |
| 13 | 10 | | | 40 | | | |
| 15 | 10 | | | 0 | | | |
| 16 | 25 | | | | | 80 | |
| 17 | 10 | | | 0 | | | |
| 18 | 10 | | | 0 | | | |
| 24 | 25 | | | | 0 | | |
| 25 | 10 | | 100 | 85 | | | |
| 39 | 50 | | | 10 | | | |
| 40 | 50 | | | 25 | | | |
| | 25 | | | | | 70 | |
| 42 | 50 | | | 15 | | | |
| 43 | 50 | | | 0 | | | |
| 44 | 25 | | | | | | 99 |
| | 12.5 | 90 | 100 | 100 | | | 100 |
| 46 | 10 | | | 0 | | | |
| 47 | 10 | | 50 | 85 | | | |
| 48 | 10 | | 45 | 100 | | | |
| 50 | 25 | 15 | 55 | 70 | | | |
| 55 | 50 | | | 0 | | | |
| 56 | 50 | | | 30 | | | |
| 57 | 50 | | | 0 | | | |
| 58 | 50 | | | 50 | | | |
| 59 | 50 | | | 30 | | | |
| 61 | 50 | | | 30 | | | |
| | 25 | 70 | | | | | |
| 65 | 12.5 | 45 | 100 | 0 | | | |
| 67 | 25 | 100 | 100 | 100 | | | 100 |
| 68 | 25 | 90 | 90 | 45 | | | 100 |
| 69 | 25 | 90 | 95 | 95 | | | 99 |
| 70 | 25 | 100 | 100 | 100 | | | 100 |
| 71 | 25 | 100 | 90 | 90 | | | 99 |
| 72 | 25 | 100 | 100 | 100 | | | 100 |
| 75 | 25 | 75 | 100 | 100 | | | 100 |
| 77 | 25 | 90 | 100 | 100 | | | 100 |
| 78 | 25 | 80 | 100 | 100 | | | 100 |
| 80 | 25 | 75 | 100 | 95 | | | 100 |
| 92 | 25 | 100 | 100 | 100 | | | 100 |
| 93 | 25 | 100 | 100 | 95 | | | 100 |
| 94 | 10 | | | 35 | | | |
| 96 | 50 | | | 95 | | | |
| 97 | 50 | | | 80 | | | |
| 98 | 50 | | | 65 | | | |
| 99 | 10 | | | 0 | | | |
| 101 | 25 | 100 | | | | 70 | 0 |
| 102 | 25 | 100 | | | | 80 | 14 |
| | 70 | | | | | | |
| 103 | 25 | | | | | 0 | |
| 109 | 10 | | | 0 | | | |
| 110 | 10 | | | 0 | | | |
| 112 | 10 | | | 0 | | | |
| 113 | 10 | | | 0 | | | |
| 114 | 10 | | | 45 | | | |
| 116 | 10 | | | 45 | | | |
| 118 | 25 | 65 | 100 | | 0 | 0 | |
| | 10 | | 95 | 5 | | | |
| 124 | 25 | | | | | | 20 |
| 126 | 25 | | | | 0 | | 0 |
| 127 | 25 | 40 | | | 0 | 100 | 0 |
| 128 | 25 | 65 | | | 0 | 100 | 0 |
| 131 | 25 | 50 | 100 | | 0 | 10 | |
| | 10 | | | 100 | | | |
| 133 | 25 | 0 | | | | 0 | |

TABLE 4-continued

RESULTS OF SYSTEMIC (UPWARD) TESTS AGAINST INSECTS AND ACARIDS

| Cmpd # | Rate PPM | CL | MBB | PA | SAW | TBW | TSM-S |
|---|---|---|---|---|---|---|---|
| 135 | 10 | | 100 | 30 | | | |
| 136 | 25 | 85 | | | | | |
| | 10 | | 100 | 15 | | | |
| 137 | 25 | 75 | 100 | | 0 | 20 | |
| | 10 | | 100 | 70 | | | |
| 138 | 25 | 75 | | | | | |
| | 10 | | 100 | 80 | | | |
| 139 | 25 | 65 | 100 | | 0 | 0 | |
| | 10 | | | 65 | | | |
| 140 | 25 | 80 | | | | | |
| 141 | 25 | 30 | 100 | | 0 | 0 | |
| | 10 | | | 85 | | | |
| 142 | 25 | 85 | | | | | |
| 143 | 25 | 80 | 100 | | 0 | 0 | |
| | 10 | | | 70 | | | |
| 144 | 25 | 90 | 100 | | 0 | 10 | |
| | 10 | | | 65 | | | |
| 145 | 25 | 60 | 100 | | | | |
| | 10 | | | 40 | | | |
| 146 | 25 | 40 | 100 | | 0 | 0 | |
| | 10 | | | 90 | | | |
| 147 | 25 | 65 | 100 | 90 | | | |
| 149 | 25 | 95 | 100 | 95 | | | |
| 150 | 25 | 70 | | | | | |
| 151 | 25 | 70 | | | | | |
| 152 | 25 | 85 | | | | | |
| | 10 | | 100 | 55 | | | |
| 156 | 25 | 100 | 100 | 90 | | | |
| 157 | 25 | | 100 | 85 | | | |
| 158 | 25 | | 100 | 100 | | | |
| 159 | 25 | 75 | 100 | 75 | | | |
| 163 | 25 | 80 | 100 | 80 | | | 100 |
| 164 | 25 | 95 | 100 | 35 | | | 100 |
| 165 | 25 | 85 | 100 | 100 | | | 99 |
| 173 | 25 | 65 | 65 | 45 | | | |
| 191 | 25 | 65 | | | 0 | 90 | 0 |
| 192 | 25 | 80 | | | | 90 | |
| 194 | 25 | 80 | | | | | |
| 200 | 25 | 95 | 100 | | 0 | 100 | |
| | 10 | | | 15 | | | |

The compounds of the present invention were tested against the root-knot nematode (*Meloidogyne incognita*), to evaluate downward systemic nematicidal activity, as follows:

The appropriate amount of technical material was dissolved in a solvent consisting of 1:1 acetone and water to provide a test solution of 2000 ppm (w/v) in concentration.

The test tomato plants (*Lycopersicum esculentum* cv. Heinz 1350) were individually grown in 10 cm fiber pots in soil consisting of a 1:1 sand:topsoil mixture amended 20% (volume) with peat moss. The plants were selected for treatment when the third trifoliate of each plant was fully developed. Immediately prior to the treatment with the test chemical the soil surface in each pot was covered with vermiculite to prevent chemical contact with the soil.

Three test plants for each test chemical were placed on a turntable inside a ventilated spray hood and rotated at approximately 30 rpm. The solution of test chemical was applied to the surface of the foliage of the test plants by pressurized spray through a fixed spray nozzle designed to provide a fine mist output. The test plants were then moved to a fully illuminated drying area where they remained for approximately two hours. The test plants were then placed in a greenhouse where the vermiculite covering the soil in each pot was carefully removed.

Approximately three days after the treatment of the test plants with the test chemicals, a trench 2 cm deep centered between the plant stem and the pot wall was formed in the soil around each test plant. A 10–15 mL aqueous suspension containing 2500–3000 eggs and juvenile root-knot nematode was syringed evenly into the trench. Upon completion of inoculation the trenches in each pot were refilled with the soil removed from them.

Fourteen to twenty-one days after inoculation the roots of the test plants were shaken free of soil, the extent of root-galling was compared to the root-galling in the untreated control plants, and the percent control was determined.

The results, utilizing an application rate of 2000 ppm and a 14 to 21 day exposure period, are shown in Table 5:

TABLE 5
Results of Systemic (Downward) Tests Against the Root-knot Nematode

| Cmpd No. | Percent Control |
| --- | --- |
| 3 | 0 |
| 6 | 0 |
| 44 | 85.0 |
| 62 | 75.0 |
| 70 | 100.0 |
| 102 | 58.3 |
| 127 | 73.3 |
| 128 | 8.3 |
| 192 | 73.3 |
| 198 | 50.0 |
| 200 | 0 |

In evaluations to determine leaf to leaf systemic insecticidal activity the compounds of the present invention were tested against the pea aphid, as follows:

The appropriate amount of technical material was dissolved in a solvent consisting of 1:9 acetone and water containing 0.5% octylphenoxypolyethoxyethanol emulsifier to provide a test solution of 4000 ppm (w/v) in concentration. A standard, 2000 ppm in concentration, and untreated controls were also included in these tests.

Two-week-old fava bean plants were transplanted into a soil consisting of a 1:1 mixture of sand and topsoil contained in 7.5 cm pots. A sufficient number of test plants were planted to allow three replicates for each test chemical.

After the plants had recovered from transplanting, the test chemical was swabbed onto both sides of the two to four mature lower leaves of the test plant. Care was taken not to apply any of the test solution to immature leaves on the test plant. The treated test plants were placed in a growth chamber where they were maintained for a 48 to 72 hour translocation period.

After this time the upper stem of the test plant with the untreated immature leaves attached was excised. Each of the excised stem and leaf segments was placed in four dram vials containing water. Each of the vials was placed in 46 ounce cups where they were supported by approximately 2.5 cm of sand in the bottom of each cup. Each stem and leaf segment was infested with 10 pea aphids. Upon completion of the infestation each cup was covered with cheese cloth. The covered cups were returned to a growth chamber where they were maintained for a 48 hours period. After this time the ability of the test chemical to move from mature fava bean leaves to immature leaves was assessed by determining the percent mortality of the pea aphid. Test chemicals providing 50% mortality or greater were termed active.

Of the compounds tested Compound 9, Compound 44, Compound 47, Compound 70, Compound 94, Compound 138, and Compound 194 were active in this test.

We claim:

1. A difluoroalkane or difluoroalkenylalkane derivative of the structural formula I

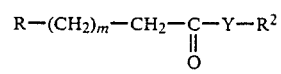

in which R is a 1,1-difluoroalkyl group of 1 to 3 carbon atoms or a 1,1-difluoroalkenyl group of 2 to 4 carbon atoms, optionally carrying a halogen substituent selected from bromine and chlorine, m is an integer which produces a carbon chain length for the group $R(CH_2)_m$ which is an even number in the range of 2 to 20, Y is $-NR^1-$, or $-O-$, $R^1$ is hydrogen or lower alkyl, and $R^2$ is:

(a) hydrogen, an alkali metal, or ammonium,
(b) alkyl of 1 to 12 carbon atoms,
(c) lower alkyl substituted with halogen, trifluoromethyl, ethenyl, difluoroethenyl ethynyl, lower alkoxy, $C_3-C_6$ cycloalkyl which may be fluoro-substituted, lower alkylcarbonyl, lower alkoxycarbonyl, hydroxycarbonyl, cyano, phenylmethylfuryl, phenoxy, halophenoxy, phenyl, halophenyl, $C_1-C_2$ alkoxyphenyl, thienyl, halothienyl, or a cyclopropyl group and a phenyl group which may be substituted with a substituent selected from halogen, methyl, trifluoromethyl and trifluoromethoxy, or a methyl group substituted with phenylmethyl and hydroxycarbonyl,
(d) phenyl which may be substituted with one to three substituents independently selected from lower alkyl, halogen, lower alkoxy, formyl, nitro, hydroxycarbonylethenyl, lower alkoxycarbonylethenyl, and lower alkylamino(lower)alkoxycarbonyl,
(e) pyridyl which may be substituted with halogen,
(f) a group of the formula $-SO_2R^3$ in which $R^3$ is phenyl or phenylmethyl in which the ring may be substituted with a substituent selected from the group consisting of lower alkyl, halogen, and lower alkoxy, thienyl, pyridyl, or lower alkyl,
(g) a group of the formula $-N=CR^4R^5$ in which $R^4$ is amino or dimethylamino and $R^5$ is phenyl or phenylmethyl optionally ring substituted with lower alkoxy or trifluoromethoxy, or thienyl,
(h) a group of the formula $-C(SR^6)=NR^7$ in which $R^6$ is lower alkyl or $F_2C=CFC_2H_4$ and $R^7$ is lower alkylcarbonyl or phenyl which may be substituted with a halogen atom,
(i) a group of the formula $-NR^8R^9$ in which $R^8$ is hydrogen or lower alkyl, $R^9$ is hydrogen, lower alkyl, alkylaminocarbonyl, phenylcarbonyl, $F_2C=CHC_3H_6C(O)-$ or acetyl,
(j) a substituent selected from fluoroethoxy, $F_2ClCCH=CHC_9H_{18}-$, $F_2C=CHC_{10}H_{20}-$, 2,2-dimethyl-2,3-dihydrobenzofuranyl, 2,2-dimethyl-2,3-dihydrobenzofuranyloxycarbonyl, dimethoxyindanyl, and

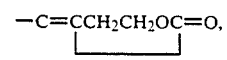

or Y and $R^2$ taken together are hydrogen or form a nitrogen containing group selected from (lower)alkenylamino, piperidyl, pyrrolidinyl, or thiomorpholinyl.

2. The compound of claim 1 in which R is selected from the group consisting of $F_2XC$, $F_2XCX^1CH$, $F_2XCCH_2X^1CH$, $F_2C=CX^2$, $F_2XCCH=CH$, and $F_2XCCH=CHX^1CH$ in which $X^2$ is hydrogen, bromine or chlorine and X and $X^1$ are bromine or chlorine.

3. The compound of claim 2 in which R is $F_2C=CH$.

4. The compound of claim 3 in which Y is $-NR^1-$.

5. The compound of claim 4 in which $R^2$ is hydrogen, lower alkyl, lower haloalkyl, propenyl, propynyl, lower alkoxyalkyl, $C_1-C_2$ alkoxycarbonyl(lower)alkyl, hydroxycarbonyl(lower)alkyl, lower cyanoalkyl, lower phenylalkyl in which the phenyl ring is unsubstituted or is substituted with halogen, lower thienylalkyl, lower halothienylalkyl, 1-carboxy-2-phenylethyl, phenyl which may be substituted with one to three substituents selected from the group consisting of lower alkyl, halogen, nitro and di(lower)alkylamino(lower)alkoxycarbonyl, pyridyl, halopyridyl, $SO_2$ substituted with a substituent selected from the group consisting of phenyl, phenylmethyl, lower alkylphenyl, halophenyl, lower alkoxyphenyl, thienyl, pyridyl, and $C_1-C_2$ alkyl, a group of the formula $-C(SR^6)=NR^7$ in which $R^6$ is lower alkyl or $F_2C=CFC_2H_4-$ and $R^7$ is lower alkylcarbonyl or halophenyl, amino, lower dialkylamino, $C_1-C_2$ alkylaminocarbonylamino, phenylcarbonylamino, difluoroethenylpropylcarbonylamino, acetyl, carbonylamino, haloethoxy, or 2,2-dimethyl-2,3-dihydrobenzofuran-7-yl-oxycarbonyl.

6. The compound of claim 3 in which Y and $R^2$ are combined to form a nitrogen containing group selected from the group consisting of dipropenylamino, piperidyl, pyrrolidinyl, and thiomorpholinyl.

7. The compound of claim 3 in which Y is $-O-$.

8. The compound of claim 7 in which $R^2$ is hydrogen, an alkali metal, ammonium, alkyl of 1 to 12 carbon atoms, lower haloalkyl, lower fluoroalkenyl, $C_5-C_6$ cycloalkyl which may be fluorinated, lower alkylcarbonyl(lower)alkyl, lower alkoxycarbonyl(lower)alkyl, hydroxycarbonylmethyl, lower cyanoalkyl, 5-benzyl-3-furylmethyl, phenoxy(lower)alkyl, halophenoxy(lower)alkyl, phenyl(lower)alkyl, halophenyl(lower)alkyl, methoxyphenyl(lower)alkyl, thienyl(lower)alkyl, halothienyl(lower)alkyl, a lower alkyl group substituted with cyclopropyl and a phenyl ring in which the phenyl ring is substituted with a substituent selected from halogen, trifluoromethyl, methyl, and trifluoromethoxy, halophenyl, or phenyl substituted with at least one substituent selected from methoxy, methyl, formyl, hydroxycarbonylethenyl, and methoxycarbonylethenyl.

9. A pesticidal composition comprising an agriculturally acceptable vehicle in admixture with an insecticidal amount of a compound of claim 1, 2, 3, 4, 5, 6, 7, or 8.

10. A method for controlling plant pests which comprises applying to the locus where control is desired an insecticidally effective amount of a compound of claim 1, 2, 3, 4, 5, 6, 7, or 8.

11. The method of claim 10 in which said compound is applied to the above ground portions of a plant for local and systemic downward activity.

12. The method of claim 10 in which said compound is applied to the root zone in which a plant is or is about to be planted for control of nematodes, soil-borne insects and foliar feeding insects and acarids.

* * * * *

UNITED STATES PATENT AND TRADEMARK OFFICE
CERTIFICATE OF CORRECTION

PATENT NO. : 4,950,666

DATED : August 21, 1990

INVENTOR(S) : Clinton J. Peake, Thomas G. Cullen, Anthony J. Martinez

It is certified that error appears in the above-identified patent and that said Letters Patent is hereby corrected as shown below:

Column 5, line 22, "115" should read --155--.

Signed and Sealed this

Sixth Day of October, 1992

Attest:

DOUGLAS B. COMER

Attesting Officer

Acting Commissioner of Patents and Trademarks